United States Patent
Meyer et al.

(10) Patent No.: US 6,740,326 B1
(45) Date of Patent: May 25, 2004

(54) TOPICAL NAIL CARE COMPOSITIONS

(75) Inventors: Hans Meyer, Reihen (CH); Hermann Wasmer, Riehen (CH)

(73) Assignee: BioEqual AG, Muttenz (CH)

( * ) Notice: Subject to any disclaimer, the term of this patent is extended or adjusted under 35 U.S.C. 154(b) by 0 days.

(21) Appl. No.: 09/786,928

(22) PCT Filed: Sep. 3, 1999

(86) PCT No.: PCT/CH99/00409

§ 371 (c)(1),
(2), (4) Date: Jun. 19, 2001

(87) PCT Pub. No.: WO00/15202

PCT Pub. Date: Mar. 23, 2000

(30) Foreign Application Priority Data

Sep. 10, 1998 (EP) ............................................ 98117114
Mar. 5, 1999 (EP) ............................................ 99104466

(51) Int. Cl.$^7$ ................................................ A61K 6/00
(52) U.S. Cl. ......................................... 424/401; 424/61
(58) Field of Search ..................... 424/61, 401, 78.37

(56) References Cited

U.S. PATENT DOCUMENTS 3,806,593 A * 4/1974 Swanbeck et al. ............ 424/28
4,710,497 A    12/1987 Heller et al. ................. 514/221
5,290,543 A *  3/1994 Ounanian et al. ........... 424/401
5,372,742 A * 12/1994 Bayless ....................... 252/170
5,968,986 A * 10/1999 Dyer ........................... 514/643

FOREIGN PATENT DOCUMENTS

| EP | 0 503 988 A1 | 9/1992 |
| EP | 0 534 810 A1 | 3/1993 |
| EP | 0 745 372 A1 | 12/1996 |
| EP | 0 770 399 A2 | 5/1997 |
| WO | WO 96/40047 A1 | 12/1996 |

OTHER PUBLICATIONS

Database EPO Doc. XP–002124817, Jun. 1998.
Abstract US Patent No. 61246113; Patent Abstracts of Japan vol. 11, No. 96, Nov. 2000.

* cited by examiner

*Primary Examiner*—Thurman K. Page
*Assistant Examiner*—Lakshmi Channavajjala
(74) *Attorney, Agent, or Firm*—Jones Day

(57) ABSTRACT

The present invention relates to water-free topical application products for the treatment of nail diseases and nail care containing one or more active substances, $C_1$–$C_4$-alkyl esters of lactic acid, malic acid, tartaric acid as carrier and optionally physiologically compatible adjuvants. The invention is also concerned with a process for the manufacture of these products and their use.

9 Claims, No Drawings

# TOPICAL NAIL CARE COMPOSITIONS

FIELD OF THE INVENTION

The present invention is in the field of topically applied nail care compositions, the process of manufacturing such compositions and the methods of using such compositions.

BACKGROUND OF THE INVENTION

The direct topical treatment of nail diseases and the nail care proceed practically free of side-effects, are very simple to carry out and cause only minimal costs. However, the essential problem of the direct topical use of nail compositions consists in carrying the active substances including nutrient and anabolic substances in sufficient amounts through the nail into the deeper situated tissue layers and into the nail root, completely destroying the pathogens present and providing the nail with nutrient and anabolic substances. With conventional products it is possible to ease the symptoms by direct topical treatment; however, in the regular case they reappear after termination of the treatment.

It has already been proposed to improve the results of the treatment with the direct topical use of active substances in that the active substances were used together with a so-called carrier, i.e. a substance which in addition to a good solubility for the active substance also possesses a good penetrability through the nail substance and the ability to transport the active substance through the nail tissue. As an example, EP-A-0 503 988 describes medicaments for the treatment of onychomycoses, which in addition to an antimycotically active substance and an aqueous medium, in which the antimycotic is at least partly soluble, contains at least one hydrophilic substance promoting the penetration of the antimycotic through the nail. In addition to a large number of compounds also lactic acid ethyl ester is mentioned as penetration promoting substance. The formulation principle described in EP-A-0 503 988 is in view of the partial water-solubility postulated for the active substance only useful for a limited number of active substances. In addition, and in view of the water content of the formulation when using hydrolyzable compounds as penetration promoting substances, such as lactic acid ethyl ester, no stable formulations can be prepared according to this principle, since such compounds decompose by hydrolysis during storage.

Up to the present no satisfactory product for topical treatment of nail diseases and for topical nail care exists, which contains a carrier guaranteeing the transport of the amount of active substance through the nail into the deeper situated nail bed and to the nail root (matrix) required for a long-term treatment result.

It is therefore the task of the present invention to solve the problems connected with the topical treatment of nail diseases and the topical nail care and to provide pharmaceutical and cosmetic products which enable a long-term treatment result.

SUMMARY OF THE INVENTION

According to the present invention water-free topical application products for the treatment of nail diseases and nail care are proposed, which have the following composition:
a) one or more active substances
b) one or more $C_1$–$C_4$-alkyl esters of lactic acid, malic acid, tartaric acid or citric acid as carrier and
c) optionally physiologically compatible adjuvants.

In an embodiment, the topical application product is characterized in that it contains an ethyl ester of lactic acid, malic acid, tartaric acid or citric acid as carrier.

In another embodiment, the topical application product is characterized in that it contains an isopropyl ester of lactic acid, malic acid, tartaric acid or citric acid as carrier.

In an embodiment, the topical application product is characterized in that it contains lactic acid ethyl ester as carrier.

In another embodiment, the topical application product is characterized in that it contains malic acid diisopropylester as carrier.

In one embodiment, the topical application product is characterized by a content of one or more active substances selected from the group consisting of antimycotics of synthetic or natural origin, antibiotics, antiseptics, corticosteroids and nutrient and anabolic substances.

In another embodiment, the topical application product is characterized by a content of one or more antimycotic active substances selected from the group consisting of (±)-cis-2,6-dimethyl-4-[2-methyl-3-(p-tert-pentyl phenyl)propyl]morpholine (amorolfin), amphotericin, 6-cyclohexyl-1-hydroxy-4-methyl-2(1H)pyridinone (ciclopirox), bisphenyl-(2-chlorophenyl)-1-imidazolylmethane (clotrimazol), 1-[2-(2,4-dichlorophenyl)-2-(4-chlorobenzyloxy)ethyl-1-imidazole (econazol), 2,4-difluoro-α,α-bis(1H-1,2,4-triazol-1-ylmethyl)benzylalcohol (fluconazol), 5-fluorocytosine (flucytosin), 7-chloro-trimethoxy-methylspiro-[benzofuran-cyclohexenp]dione-(griseofulvin), 1-[2,4-dichloro-β-(2,6-dichlorobenzyloxy)phenethyl]-imidazole (isoconazol), (±)-1-sec-butyl-4-{4-[4-(4-{[2R*, 4S*)-2-(2,4-dichlorophenyl)-2-(1,2,4-triazol-1-ylmethyl)-1,3-dioxolan-4-yl]methoxy}phenyl)-1-piperazinyl]phenyl}-4,5-dihydro-1,2,4-triazol-5-one (itraconazol), (±)-cis-1-acetyl-4-{4-([2-(2,4-dichlorophenyl)-2-(1H-imidazol-1-ylmethyl)-1,3-dioxolan-4-yl]methoxy)phenyl}piperazine (ketoconazol), 1-[2,4-dichloro-β-(2,4-dichlorobenzyloxyl)-phenethyl]-imidazole (miconazol), (E)-N-cinnamyl-N-methyl-1-naphthylmethylamine (naftifin), nystatin, (E)-N-(6,6-dimethyl-2-hepten-4-ynyl)-N-methyl-1-naphthylmethylamine (terbinafin), 1[2-{(2-chloro-3-thienyl)methoxy}-2(2,4dichlorophenyl)ethyl]-1H-imidazole (tioconazol), O-2-naphthyl-N-methylN(3-tolyl)-thiocarbamate (tolnaftat) and α-(2,4-difluorophenyl)-5-fluoro-β-methyl-α-(1H-1,2,4-triazol-1-ylmethyl)-4-pyrimidinethanol (voriconazol).

In one embodiment, the topical application product is characterized by a content of one or more antibacterially or antimycotically active substances selected from tea tree oil, lavender oil, thuja oil and leaf extract of the nim tree.

In one embodiment, the topical application product is characterized by a content of one or more antibiotic substances selected from α-amino-4-hydroxybenzylpenicillin (amoxicillin), D-(−)-α-aminobenzylpenicillin (ampicillin), 3,3-dimethyl-7-oxo-6-phenylacetamido-4-thia-1-azabicyclo-[3.2.0]-heptan-2-carboxylic acid (benzylpenicillin), benzylpenicillin-benzathin, 3-chloro-7-D-(2-phenylglycinamido)-cephalosporanic acid (cefaclor), 7β-[D-2-amino-(4-hydroxyphenyl)-acetylamino]-3-methylcephalosporanic acid (cefadroxil), amino-phenylacetamido-methyl-cephalosporanic acid (cefalexin), D(−)-threo-2-dichloroacetamido-1-(4-nitrophenyl)-1,3-propanediol (chloramphenicol), 1-cyclopropyl-6-fluoro-1,4-dihydro-4-oxo-7-(piperazinyl)3-quinolinecarboxylic acid (ciprofloxacin), (Z)-(2R,5R)-3-(2-hydroxyethylidene)-7- oxo-4-oxa-1-azabicyclo[3.2.0]heptan-2-carboxylic acid (clavulanic acid), 7-chloro-7-desoxy-1-lincomycin (clindamycin), 6-desoxy-5-hydroxytetracycline (doxycyclin), 1-ethyl-6-fluoro-1,4-dihydro-4-oxo-7-(1-piperazinyl)-1,8-naphthyridin-3-carboxylic acid (enoxacin), erythromycin, 3-(2-chloro-6-fluorophenyl)5-methyl-4-isoxazolyl-penicillin (flucloxacillin), kanamycin, lincomycin, 7-dimethylamino-6-desoxy-desmethyltetracycline (minocycline), 6-(2-ethoxy-1-naphthamido)-penicillin (nafcillin), 1-ethyl-1,4-dihydro-7-methyl-4-oxo-1,8-naphthyridin-3-carboxylic acid (nalidixic acid), neomycin, 1-ethyl-6-fluoro-1,4-dihydro-4-oxo-7-(1-piperazinyl)-3-quinolinecarboxylic acid (norfioxacin), (±)-9-fluoro-2,3-dihydro-3-methyl-10-(4-methyl-1-piperazinyl)-7-oxo-7H-pyrido[1,2,3-de][1,4]benzoxazin-6-carboxylic acid (ofloxacin), 6-(5-methyl-3-phenyl-4-isoxazolcarboxamido)penicillanic acid (oxacillin), 6-phenoxyacetylamino-penicillanic acid (phenoxymethylpenicillin) and 4-dimethylamino-octahydro-pentahydroxy-1,11-dioxo-6-methyl-naphtacene-2-carbamide (tetracyclin).

In another embodiment, the topical application product is characterized by a content of one or more antiseptically active substances selected from alkylbenzyldimethylammonium chloride (benzalkonium chloride), N-benzyl-N,N-dimethyl-2-{2-[p-(1,1,3,3, -tetramethylbutyl)-phenoxy]ethoxy}ethylammonium hydroxide (benzethonium chloride), cetyltrimethylammonium hydroxide (cetrimonium bromide), 1,1'-hexamethylen-bis-[5-(p-chlorophenyl)biguanide](chlorohexidine), $N^1,N^1$-decamethylen-bis-(4-aminoquinaldinium hydroxide) (dequalinium chloride), N-(4-chlorophenyl)-N'-(3, 4dichlorophenyl)urea (triclocarbane) and 5-chloro-2-(2,4-dichlorophenoxy)phenol (triclosan).

In one embodiment, the topical application product is characterized by an active ingredient content of one or more corticosteroids selected from 9α-chloro-16β-methylprednisolone (beclomethasone), 9-fluoro-11β,17,21-trihydroxy-16β-methyl-1,4-pregnadien-3,20-dione (betamethason), 21-chloro-9-fluoro-11β,17-dihydroxy-16β-methyl-1,4-pregnadien-3,20-dione (clobetasol), 17,21-dihydroxy-pregn-4-en-3,11,20-trione (cortisone), 11β,16α, 17α,21-tetrahydroxy-1,4-pregnadien-3,20-dione-16,17-acetone acetal (desonid), 9-fluoro-11β-17,21-trihydroxy-16α-methylpregna-1,4-dien-3,20-dione (dexamethason), 9α,11β-dichloro-6α-fluoro-21-hydroxy-16α,17α-(isopropylidenedioxy)-pregna-1,4-dien-3,20-dione (flucloronid), 6α,9α-difluoro-16α,17α-isopropylidenedioxy-corticosterone (fluocinolonacetonide), 6α,9α-difluoro-16α,17α-isopropylidenedioxy-corticosterone-acetate (fluocinonid), 6α-fluoro-11β,21-dihydroxy-16α,17-isopropylidenedioxy-4-pregnen3,20-dione (fludroxycortide), 3-(2-chloroethoxy)-9α-fluoro-6-formyl-11,21-dihydroxy-16α,17α-isopropylidenedioxypregna-3,5-dien-20-one (formocortal), 21-chloro-9α-fluoro-11β-hydroxy-16α,17α-isopropylidenedioxy-4-pregnen-3,20-dione (halcinonide), 17α-hydroxycorticosterone (hydrocortisone), 11β,17,21-trihydroxy-6α-methyl-1,4-pregnadien-3,20-dione (methylprednisolone), 11β,17,21-trihydroxy-pregna-1,4-dien-3,20-dione (prednisolone), 17α, 21-dihydroxypregna-1,4-dien-3,11,20-trione (prednisone), 9-fluoro-16α-hydroxyprednisolone (triamcinolone) and triamcinolone-16α,17-acetonide (triamcinolone acetonide).

In another embodiment, the topical application product is characterized by a content of the nutrient and anabolic substance L-proline.

In one embodiment, the topical application product is characterized by a content of L-proline in combination with one or more further nutrient and anabolic substances selected from the group of the amino acids, the vitamins and the mineral substances.

In another embodiment, the topical application product is characterized by a content of L-proline in combination with one or more nutrient and anabolic substances selected from lysine, cystein, gelatine, biotin, panthenol, dexpanthenol and inorganic or organic calcium, magnesium or zinc compounds.

In one embodiment, the topical application product is characterized by a content of one or more adjuvants from the group consisting of terpenes or terpene-containing oils, alcohols, ketones, fatty acid esters, polyglycols, tensides, urea, antioxidants and complexing agents.

In another embodiment, the topical application product is characterized in that it contains 0.01 to 20 percent by weight of one or more active substances, 1 to 99.99 percent by weight of $C_1$–$C_4$-alkyl esters of lactic acid, malic acid, tartaric acid or citric acid and 0 to 98.99 percent by weight of the adjuvants.

In one embodiment, the process for the manufacture of topical application products is characterized in that one or more $C_1$–$C_4$-alkyl esters of lactic acid, malic acid, tartaric acid or citric acid and, if desired, one or more adjuvants are homogenously mixed, subsequently one or more active substances are dissolved in the mixture with stirring and optional heating, and stirring is continued until a homogenous solution is obtained.

In another embodiment, the process for the manufacture of a topical application product is characterized in that the solution is further processed with the addition of physiologically acceptable formulation adjuvants to topical application forms.

The invention also relates to the use of a topical application product for the treatment, prevention, after-treatment and supporting treatment of nail diseases and periungual diseases.

The invention further relates to the use of a topical application product for nail care.

The invention still further relates to the use of a topical application product for the treatment of mycotic infections of the hooves, paws and claws of pets and domestic animals.

DETAILED DESCRIPTION OF THE INVENTION

It is therefore the task of the present invention to solve the problems connected with the topical treatment of nail diseases and the topical nail care and to provide pharmaceutical and cosmetic products which enable a long-term treatment result.

According to the present invention water-free topical application products for the treatment of nail diseases and nail care are proposed, which have the following composition:

a) one or more active substances b) one or more $C_1$–$C_4$-alkyl esters of lactic acid, malic acid, tartaric acid or citric acid as carrier and c) optionally physiologically compatible adjuvants.

For the water-free topical application products of the invention principally all active substances of synthetic or natural origin are considered, which are active in the treatment of nail and periungual diseases. In addition, nutrient and anabolic substances, which are effective in the nail care, are considered as active substances.

Suitable active substances which can be contained in the products of the invention are antimycotics of synthetic and natural origin, antibiotics, antiseptics, corticosteroids, nutrient and anabolic substances as well as a combinations of the mentioned active substances. Specific examples of such active substances are:

- antimycotics and their physiologically acceptable salts, such as e.g. (±)-cis-2,6-dimethyl-4-[2-methyl-3-(p-tert-pentyl-phenyl)propyllmorpholine(amorolfin), amphotericin, 6-cyclohexyl-1-hydroxy-4-methyl-2 (1H)pyridinone (ciclopirox), bis-phenyl-(2-chlorophenyl)-1-imidazolylmethane (clotrimazol), 1-[2-(2,4-dichlorophenyl)-2-(4-chlorobenzyloxy)-ethyl]imidazole (econazol), 2,4-difluoro-α,α-bis(1H-,2,4-triazol-1-ylmethyl)benzylalcohol (fluconazol), 5-fluorocytosine (flucytosin), 7-chloro-trimethoxy-methylspiro-[benzofuran-cyclohexen]-dione (griseofulvin), 1-[2,4-dichloro-β-(2,6-dichlorobenzyloxy)-phenethyl]-imidazole (isoconazol), (±)-1-sec-butyl-4-{4-[4-(4-{[(2R*,4S*)-2-(2,4-dichlorophenyl)-2-(1,2,4-triazol-1-ylmethyl)-1,3-dioxolan-4-yl]methoxy}-phenyl)-1-piperazinyl] phenyl}-4,5-dihydro-1,2,4-triazol-5-one (itraconazol), (±)-cis-1-acetyl-4-{4-([2-(2,4-dichlorophenyl)-2-(1H-imidazol-1-ylmethyl)-1,3-dioxolan-4-yl]methoxy) phenyl}piperazine (ketoconazol), 1-[2,4-dichloro-β-(2,4-dichlorobenzyloxyl)-phenethyl]-imidazole (miconazol)(E)-N-cinnamyl-N-methyl-1-naphthylmethylamine (naftifin), nystatin, (E)-N-(6,6-dimethyl-2-hepten-4-ynyl)-N-methyl-1-naphthylmethylamine (terbinafin), 1[2-{(2-chloro-3-thienyl)methoxy}-2-(2,4-dichlorophenyl)ethyl]-1H-imidazole (tioconazol), O-2-naphthyl-N-methyl-N-(3-tolyl)-thiocarbamate (tolnaftat) and α-(2,4-difluorophenyl)-5-fluoro-β-methyl-α-(1H-1,2,4-triazol-1-ylmethyl)-4-pyrimidinethanol (voriconazol).
- antimycotics of natural origin, such as e.g. etheric oils and plant extracts.
- antibiotics and their physiologically acceptable salts, such as e.g. α-amino-4-hydroxybenzylpenicillin (amoxicillin), D-(-)-α-aminobenzylpenicillin (ampicillin), 3,3-dimethyl-7-oxo-6-phenylacetamido-4-thia-1-azabicyclo-[3.2.0]-heptan-2-carboxylic acid (benzylpenicillin), benzylpenicillin-benzathin, 3-chloro-7-D-(2-phenylglycinamido)-cephalosporanic acid (cefaclor), 7β-[D-2-amino-(4-hydroxyphenyl)-acetylamino]-3-methyl-cephalosporanic acid (cefadroxil), amino-phenylacetamido-methyl-cephalosporanic acid (cefalexin), D(-)-threo-2-dichloroacetamido-1-(4-nitrophenyl)-1,3-propanediol (chloramphenicol), 1-cyclopropyl-6-fluoro-1,4-dihydro-4-oxo-7-(piperazinyl)-3-quinolinecarboxylic acid (ciprofloxacin), (Z)-(2R, 5R)-3-(2-hydroxyethylidene)-7-oxo-4-oxa-1-azabicyclo[3.2.0] heptan-2-carboxylic acid (clavulanic acid), 7-chloro-7-desoxy-lincomycin (clindamycin), 6-desoxy-5-hydroxytetracycline (doxycyclin), 1-ethyl-6-fluoro-1,4-dihydro-4-oxo-7-(1-piperazinyl)-1,8-naphthyridin-3-carboxylic acid (enoxacin), erythromycin, 3-(2-chloro-6-fluorophenyl)-5-methyl-4-isoxazolyl-penicillin (flucloxacillin), kanamycin, lincomycin, 7-dimethylamino-6-desoxy-6-desmethyltetracycline (minocycline), 6-(2-ethoxy-1-naphthamido)-penicillin (nafcillin), 1-ethyl-1,4-dihydro-7-methyl-4-oxo-1,8-naphthyridin-3-carboxylic acid (nalidixic acid), neomycin, 1-ethyl-6-fluoro-1,4-dihydro-4-oxo-7-(1-piperazinyl)-3-quinolinecarboxylic acid (norfloxacin), (±)-9-fluoro-2,3-dihydro-3-methyl-10-(4-methyl-1-piperazinyl)-7-oxo-7H-pyrido[1,2,3-de][1,4] benzoxazin-6-carboxylic acid (ofloxacin), 6-(5-methyl-3-phenyl-4-isoxazolcarboxamido)penicillanic acid (oxacillin), 6-phenoxyacetylamino-penicillanic acid (phenoxymethylpenicillin) and 4-dimethylamino-octahydro-pentahydroxy-1,11-dioxo-6-methyl-naphtacene-2-carbamide (tetracyclin).
- antiseptics such as e.g. alkylbenzyldimethylammonium chloride (benzalkonium chloride), N-benzyl-N,N-dimethyl-2-{2-[p-(1,1,3,3,-tetramethylbutyl)-phenoxy]-ethoxy}-ethylammonium hydroxide (benzethonium chloride), cetyltrimethylammonium hydroxide (cetrimonium bromide), 1,1'-hexamethylen-bis-[5-(p-chlorophenyl)-biguanide](chlorohexidine), $N^1$, $N^1$-decamethylen-bis-(4-aminoquinaldinium hydroxide) (dequalinium chloride), N-(4-chlorophenyl)-N'-(3,4-dichlorophenyl)urea (triclocarbane) and 5-chloro-2-(2,4-dichlorophenoxy) phenol (triclosan).
- corticosteroids and their physiologically acceptable salts, such as e.g. 9α-chloro-16β-methylprednisolone (beclomethasone), 9-fluoro-11β,17,21-trihydroxy-16β-methyl-1,4-pregnadien-3,20-dione (betamethason), 21-chloro-9-fluoro-11β,17-dihydroxy-16β-methyl-1,4-pregnadien-3,20-dione (clobetasol), 17,21-dihydroxy-pregn-4-en-3,11,20-trione (cortisone), 11β,16α,17α,21-tetrahydroxy-1,4-pregnadien-3,20-dione-16,17-acetone acetal (desonid), 9-fluoro-11β-17,21-trihydroxy-16α-methylpregna-1,4-dien-3,20-dione (dexamethason), 9α,11β-dichloro-6α-fluoro-21-hydroxy-16α,17α-(isopropylidenedioxy)-pregna-1,4-dien-3,20-dione (flucloronid), 6α,9α-difluoro-16α,17α-isopropylidenedioxy-corticosterone (fluocinolonacetonide), 6α,9α-difluoro-16α,17α-isopropylidenedioxy-corticosterone-acetate (fluocinonid),6α-fluoro-11β, 21-dihydroxy-16α,17-isopropylidenedioxy-4-pregnen-32,0-dione (fludroxycortide), 3-(2-chloroethoxy)-9α-fluoro-6-formyl-11β,21-dihydroxy-16α,17α-isopropylidenedioxypregna-3,5-dien-20-one (formocortal), 21-chloro-9α-fluoro-11β-hydroxy-16α,17α-isopropylidenedioxy-4-pregnen-3,20-dione (halcinonide), 17α-hydroxycorticosterone (hydrocortisone), 11β,17,21-trihydroxy-6α-methyl-1,4-pregnadien-3,20-dione (methylprednisolone), 11β,17,21-trihydroxy-pregna-1,4-dien-3,20-dione (prednisolone), 17α,21-dihydroxypregna-1,4-dien-3,11,20-trione (prednisone), 9-fluoro-16α-hydroxyprednisolone (triamcinolone) and triamcinolone-16α,17-acetonide (triamcinolone acetonide).
- nutrient and anabolic substances such as e.g. 2-pyrrolidinecarbolic acid (L-proline).

Preferred antimycotics according to the present invention are bis-phenyl-(2-chlorophenyl)-1-imidazolylmethane (clotrimazol), 1-[2,4-dichloro-β-(2,6-dichlorobenzyloxy)-phenethyl]imidazole (isoconazol), 2,4-difluoro-α,α,-bis (1H-1,2,4-triazol-1-ylmethyl)benzyl alcohol (fluconazol), (±)-1-sec-butyl-4-{4-[4-(4-{[2R*,4S*)-2-(2,4-dichlorophenyl)-2-(1,2,4-triazol-1-ylmethyl)-1,3-dioxolan-4-yl]methoxy}phenyl)-1-piperazinyl]phenyl}-4,5-dihydro-1,2,4-triazol-5-one (itraconazol), (±)-cis-1-acetyl-4-{4-([2-(2,4-dichlorophenyl)-2-(1H-imidazol-1-ylmethyl)-1,3-dioxolan-4-yl]methoxy)phenyl}piperazine (ketoconazol), 1-[2,4-dichloro-β-(2,4-dichlorobenzyloxyl)-phenethyl]-imidazole (miconazol), (E)-N-(6,6-dimethyl-2-hepten-4- ynyl)-N-methyl-1-naphtylmethylamine (terbinafin),α-(2,4-difluorophenyl)-5-fluoro-β-methyl-α-(1H-1,2,4-triazol-1-ylmethyl)-4-pyrimid methanol (voriconazol).

Particularly preferred antimycotics according to the present invention are bis-phenyl-(2-chlorophenyl)-1-imidazolylmethane (clotrimazol), 1-[2,4-dichloro-β-(2,6-dichlorobenzyloxy)-phenethyllimidazole (isoconazol), (±)-1-sec-butyl-4-{4-[4-(4-{[2R*,4S*)-2-(2,4-dichlorophenyl)-2-(1,2,4-triazol-1-ylmethyl)-1,3-dioxolan-4-yl]methoxy}phenyl)-1-piperazinyl]phenyl}-4,5-dihydro-1,2,4-triazol-5-one (itraconazol), (±)-cis-1-acetyl-4-{4-([2-(2,4-dichlorophenyl)-2-(1H-imidazol-1-ylmethyl)-1,3-dioxolan-4-yl]methoxy)phenyl}piperazine (ketoconazol).

Preferred antimycotics of natural origin are tea tree oil (Melaleuca alternifolia), lavender oil (Lavandula officinalis chaix) and leaf extract of the nim tree (Azadirachta indica). These natural antimycotics can be used as single active substances or as combinations of several such active substances. A preferred combination of active ingredients is a mixture of lavender oil, tea tree oil and leaf extract of the nim tree.

Preferred antiseptics are e.g. 1,1'-hexamethylene-bis-[5-(p-chlorophenyl)-biguanide](chlorohexidine).

Preferred corticosteroids are 11β,16α,17α,21-tetrahydroxy-1,4-pregnadien-3,20-dione-16,17-acetone acetal (desonid), 9α,11β-dichloro-6α-fluoro-21-hydroxy-16α,17α-(isopropylidenedioxy)-pregna-1,4-dien-3,20-dione (flucloronid), 6α,9αa-difluoro-16α,17α-isopropylidenedioxy-corticosterone (fluocinolonacetonide), 6α,9α-difluoro-16α,17α-isopropylidenedioxy-corticosterone-acetate (fluocinonide), 6α-fluoro-11β,21-dihydroxy-16α,17-isopropylidenedioxy-4pregnen3,20-dione (fludroxycortide), 3-(2-chloroethoxy)-9α-fluoro-6-formyl-11β,21-dihydroxy-16α,17α-isopropylidenedioxypregna-3,5-dien-20-one (formocortal), 21-chloro-9α-fluoro-11β-hydroxy-16α,17α-isopropylidenedioxy-4-pregnen-3,20-dione (halcinonid), triamcinolone-16α,17α-acetonide (triamcinolone acetonide).

Specific examples of combinations of active substances are:
- combinations of corticosteroids with antimycotics, antibiotics or antiseptics. A preferred combination is e.g. (±)-cis-1-acetyl-4-{4-([2-(2,4-dichlorophenyl)-2-(1H-imidazol-1-ylmethyl)-1,3-dioxolan-4-yl]methoxy)phenyl}piperazine (ketoconazol) and 11β,16α,17α,21-tetrahydroxy-1,4-pregnadien-3,20-dione-16,17-acetone acetal (desonide).
- combinations of antimycotics of synthetic origin with antimycotics of natural origin. A preferred combination is bis-phenyl-(2-chloro-phenyl)-1-imidazolylmethane (clotrimazol) with tea tree oil.
- combinations of various antimycotics of natural origin. A preferred combination is lavender oil, tea tree oil and leaf extract of the nim tree.
- combinations of 2-pyrrolidine carboxylic acid (L-proline) with one or more further nutrient and anabolic substances selected from the group of the amino acids, the vitamins and the mineral substances. Preferred combinations of 2-pyrrolidine carboxylic acid (L-proline) with one or more nutrient and anabolic substances are combinations with (S)-2,6-diaminohexanoic acid (lysine), (R)-2-amino-3-mercaptopropionic acid (cystein), gelatine, cis-2-(4-carboxybutyl)-3,4-ureidotetrahydrothiophene (biotin), (±)-2,4-dihydroxy-N-(3-hydroxypropyl)3,3-dimethylbutyric acid (panthenol), D(+)-2,4-dihydroxy-N-(3-hydroxypropyl)3,3-dimethylbutyric acid (dexpanthenol) and inorganic or organic calcium, magnesium or zinc compounds.

With L-proline an anabolic substance was found, which has proven particularly suitable for nail anabolism and for nail care. L-proline was up to the present only mentioned as optional component of cosmetic products for nail care which contain a sulfurized amino acid or a derivative thereof as active component (EP-A-0 534 810).

The above-mentioned substances are in the following identified with the corresponding trivial name, entered in brackets in the above enumeration.

The $C_1$–$C_4$-alkyl esters used as carriers comprise the methyl, ethyl, n-propyl, isopropyl, n-butyl, sec.-butyl, isobutyl and tert.-butyl esters. In the esters of the polybasic acids malic acid, citric acid and tartaric acid the $C_1$–$C_4$-alkyl groups contained in the ester groups can be the same or different. In the aforementioned polybasic acids all carboxylic groups or only a part of the carboxylic groups can be esterified. In consequence, also the corresponding malic acid and tartaric acid mono alkyl esters are considered in addition to malic acid and tartaric acid di-$C_1$–$C_4$-alkyl esters. Of the $C_1$–$C_4$-alkyl esters of citric acid the corresponding mono-, di- and tri-alkyl esters are suitable. Preferred esters are the ethyl esters. Further preferred esters are the isopropyl esters. A preferred single compound is lactic acid ethyl ester. Further preferred single compounds are malic acid diethylester and malic acid di-isopropylester.

The topical application products according to the invention can in addition to one or more active substances and one or more $C_1$–$C_4$-alkyl esters of lactic acid, malic acid, tartaric acid or citric acid as carriers also contain physiologically compatible adjuvants. Suitable adjuvants of this kind are e.g. terpenes or terpene containing oils, alcohols, ketones, fatty acid esters, polyglycols, tensides, urea, antioxidants and complexing agents.

Suitable terpenes are acyclic, monocyclic and bicyclic terpenes as well as oils containing these terpenes. Examples of acyclic terpenes are acyclic terpene hydrocarbons, such as e.g. myrcene, acyclic terpene alcohols, such as e.g. citronellol and geraniol, as well as acyclic terpene aldehydes and ketones, such as e.g. citral, α-ionone and β-ionone. Examples of monocyclic terpenes are monocyclic terpene hydrocarbons, such as e.g. α-terpinene, γ-terpinene and limonene, monocyclic terpene alcohols such as e.g. thymol, menthol, cineol and carvacrol as well as monocyclic terpene ketones such as e.g. menthone and carvone. Examples of bicyclic terpenes are terpenes from the carane group such as e.g. carone, terpenes from the pinane group, such as e.g. α-pinene and β-pinene as well as terpenes from the bornane group such as e.g. campher and borneol. Particularly suitable terpenes are monocyclic terpene alcohols such as e.g. thymol and menthol. Examples for suitable oils containing terpenes are peppermint oil, cardamom oil, geranium oil, rose oil, thuja oil and thyme oil. Particularly suitable oils are peppermint oil, lavender oil and thyme oil.

Suitable alcohols are branched or unbranched alcohols with 1 to 3 hydroxy groups and 2 to 6 carbon atoms, the hydroxy groups optionally being partly or completely etherified or esterified. Particularly suitable alcohols are ethanol, 1-propanol, 2-propanol (isopropanol), 1,2-propanediol (propylene glycol), 2-phenylethanol (phenylethyl alcohol), 1-butanol (butyl alcohol), ethyleneglycol monomethylether (methoxy ethanol), ethylene glycol monophenylether (phenoxyethanol), 1,2,3-trihydroxypropane (glycerin), ethylacetate, butylacetate, glycerin diacetate (diacetin) and glycerin triacetate (triacetin).

As suitable ketones e.g. acetone and methylethyl ketone (2-butanone) are considered.

As fatty acid esters esters of saturated or unsaturated, branched or unbranched fatty acids with 8 to 21 carbon atoms are suitable, the alcohol component comprising branched and unbranched alcohols with 1 to 6 carbon atoms. Particularly suitable fatty acid esters are tridecane carboxylic acid isopropylester, tetradecane carboxylic acid isopropyl ester (isopropylmyristate), pentadecane carboxylic acid methylester and 9-octadecenoic acid glycerin monoester (glycerin monooleate).

A suitable polyglycol is e.g. polyglycol 400.

Suitable tensides are e.g. non-ionogenic surface active substances. Particularly suitable tensides are partial fatty acid esters of sorbitan (span), partial fatty acid esters of polyoxyethylene sorbitan (tween), fatty acid esters of polyoxyethylene (myrj) and fatty alcohol ethers of polyoxyethylene (brij).

Suitable antioxidants are e.g. butylhydroxytoluene (BHT), butyl-4-methoxyphenol (BHA), tocopherols and ascorbates.

As complexing agents e.g. ethylene diamine tetraacetic acid (EDTA) and disodium-ethylene diamine tetraacetic acid ($Na_2$-ETDA) are suitable.

As topical application products according to the invention e.g. solutions, tinctures, emulsions, gels, salves, creams and pastes come into consideration. Preferred topical application forms are solutions.

The invention further concerns a process for the manufacture of the topical application products of the invention, which is characterized in that the lactic acid esters and one or more adjuvants are homogenously mixed, subsequently one or more active substances are dissolved in the mixture with stirring and optional heating (up to a maximum of 80° C.) and stirring is continued until a homogenous solution is obtained. The solution obtained is preferably used directly as such for topical application. However, the solution can also be converted into another topical application form by the addition of further physiologically acceptable formulation adjuvants with the aid of conventional solution, mixing and suspension procedures.

Preferably, the topical application products according to the invention are used in the form of solutions. Preferred topical application products according to the present invention contain

| | |
|---|---|
| 0.01 to 20% by weight | one ore more active substances, |
| 1 to 99.99% by weight | one or more $C_1$–$C_4$-alkyl esters of lactic acid, malic acid, tataric acid or citric acid and |
| 0 to 98.99% by weight | one or more physiologically compatible adjuvants. |

The invention moreover concerns the use of the topical application products according to the invention for treatment, prevention, after-treatment and supporting treatment of nail diseases and periungual diseases as well as for nail care. Furthermore, the present invention concerns the use of the products of the invention for the treatment of mycotic infections of the hooves, paws and claws of pets and domestic animals.

Topical application products containing antimycotics are e.g. suitable for the following indications:

treatment, prevention and after-treatment of onychomycoses, caused by dermatophytes, yeasts or fungi or mixed infections treatment, prevention and after-treatment of nail-fungus infections in patients with psoriasis, diabetes or AIDS supporting treatment of periungual nail infections such as e.g. Candida paronychium.

Topical application products containing antibiotics are suitable e.g. for the following indications:

support of the treatment and/or prevention of nail and periungual infections caused by bacteria.

Topical application products containing antiseptics are suitable e.g. for the following indications:

treatment and prevention of nail and periungual infections caused by unspecific or not identified pathogens.

Topical application products containing corticosteroids or combinations of corticosteroids with antimycotics, antibiotics or antiseptics are suitable e.g. for the following indications:

treatment, prevention, after-treatment or supporting treatment of nail psoriasis or other inflammatory nail and periungual conditions.

The pharmaceutic topical application products according to the invention are suitable for the treatment of nail diseases and periungual diseases on toenails and fingernails, as well as for the treatment of diseases of the hooves, paws and claws of pets and domestic animals. The frequency of application of the pharmaceutical products depends on the degree and the localization of the disease. In general, application once to three times a day is sufficient. The solution is then directly applied onto the diseased nail or to the hoof, paw or claw and if required, on the surrounding skin areas concerned. The therapy should be continued for about another two weeks after the symptoms have ceased, in order to prevent a relapse.

The cosmetic topical application products according to the invention containing one or more nutrient and anabolic substances are suitable for nail care such as e.g. in nail atrophies on toenails and fingernails. Nail atrophies include e.g. fragile, brittle and thin nails as well as dotted or streaky white spots. The preparation is applied upon the cosmetically unsightly nail(s) and if required also on the surrounding skin area. The frequency of application of the preparation depends on the degree and the localization of the atrophy. In general, use once or twice a day is sufficient.

The topical application products of the invention have the advantage that they penetrate the diseased nail together with the active substance within a few days and display their action in the nail bed and the nail root. Through the more rapid onset of the effect and the better penetration, the treatment of nail diseases is as a rule terminated after about two to three months. In this way patient-compliance is clearly improved, since the long duration of treatment required in other methods of treatment is substantially shortened. With diseased skin, in particular periungual skin areas, the healing process and the nursing effect set in faster, since the active substance penetrates sufficiently and rapidly into the skin. The nail care should as a rule be carried out for one month. For maintenance of the healthy nail substance the nail care substance can also be used over a longer period of time.

EXAMPLES

The present invention is illustrated by the following examples:

Example 1

Clotrimazol Solution 1%

| | |
|---|---|
| Lactic acid ethyl ester | 20.0 ml |
| Urea | 2.0 g |
| Clotrimazol | 1.0 g |
| Lactic acid ethyl ester | ad 100.0 ml |

Urea is dissolved in 20 ml of lactic acid ethyl ester with stirring and heating (ca. 50° C.) in a 100 ml flask. Clotrimazol is added with stirring to the above solution subsequently lactic acid ethyl ester is added totalling 100 ml. Stirring is continued until a homogenous solution is formed.

Example 2

Clotrimazol-tea Tree Oil Solution 1%+10%

| | |
|---|---|
| Lactic acid ethyl ester | 20.0 ml |
| Urea | 2.0 g |
| Clotrimazol | 1.0 g |
| Tea tree oil | 10.0 g |
| Lactic acid ethyl ester | ad 100.0 ml |

Urea is dissolved in 20 ml of lactic acid ethyl ester with stirring and heating (ca. 50° C.) in a 100 ml flask. Subsequently clotrimazol and tea tree oil are added with stirring to the above solution, and lactic acid ethyl ester is added totalling 100 ml. Stirring is continued until a homogenous solution is formed.

Example 3

Tea Tree Oil Solution 30%

| | |
|---|---|
| Lactic acid ethyl ester | 44.0 g |
| Tea tree oil | 30.0 g |
| Lavender oil | 6.0 g |
| Propylene glycol | 20.0 g |

All substances are weighed in a beaker and stirred until a homogenous solution is formed.

Example 4

Nim Extract-tea Tree Oil Solution 12%

| | |
|---|---|
| Nim extract | 2.0 g |
| Propylene glycol | 22.0 g |
| Lactic acid ethyl ester | 63.0 g |
| Tea tree oilio | 10.0 g |
| Lavender oil | 5.0 g |

Nim extract is dissolved in propylene glycol with stirring. Subsequently the remaining substances are added. The mixture is stirred until a homogenous solution is formed.

Example 5

Proline-solution 1.5%

| | |
|---|---|
| L-proline | 1.5 g |
| Propylene glycol | 65.0 g |
| Lactic acid ethyl ester | 33.5 g |

L-proline is dissolved in propylene glycol with stirring and heating. Subsequently, lactic acid ethyl ester is added, and stirring is continued until a homogenous solution is formed.

Example 6

| | |
|---|---|
| L-proline | 2.0 g |
| Malic acid diethyl ester | 98.0 g |

L-proline is added to malic acid diethyl ester with stirring, and stirring is continued until complete dissolution.

Example 7

In the following table further compositions of the invention are shown, which are obtained using each 50.0 g of a hydroxy carboxylic acid $C_1$–$C_4$-alkyl ester as carrier according to the invention and each 1.0 g of active substance. For the manufacture of the compositions the active substance was added to the hydroxy carboxylic ester with stirring at room temperature or slightly increased temperature (~30° C.–50° C.). Depending on the active ingredient a clear, immediately useful solution is formed after 1–5 hours of stirring.

| Active ingredient | Hydroxy carboxylic acid ester |
|---|---|
| Clotrimazol | Lactic acid ethyl ester |
| Isoconazol | Lactic acid ethyl ester |
| Ketoconazol | Lactic acid ethyl ester |
| Itraconazol | Lactic acid ethyl ester |
| Clotrimazol | Citric acid triethyl ester |
| Isoconazol | Citric acid triethyl ester |
| Ketoconazol | Citric acid triethyl ester |
| Itraconazol | Citric acid triethyl ester |
| Clotrimazol | Malic acid diisopropyl ester |
| Isoconazol | Malic acid diisopropyl ester |
| Ketoconazol | Malic acid dusopropyl ester |
| Itraconazol | Malic acid diisopropyl ester |

Example 8

In the following table further compositions of the invention are shown, which are obtained using each 88.0 g of a hydroxy carboxylic acid $C_1$–$C_4$-alkyl ester used according to the invention as carrier and 12.0 g of an active substance combination of 5 g of lavender oil, 5 g of tea tree oil and 2 g of leaf extract of the nim tree. The compositions are prepared by stirring of the active substance combinations in the hydroxy carboxylic acid ester at room temperature. The compositions so obtained are immediately useful.

| Active ingredient | Hydroxy carboxylic acid ester |
| --- | --- |
| Lavender oil/tea tree oil/leaf extract of nim tree | Lactic acid ethyl ester |
| Lavender oil/tea tree oil/leaf extract of nim tree | Citric acid triethyl ester |
| Lavender oil/tea tree oil/leaf extract of nim tree | Malic acid diisopropyl ester |

What is claimed is:

1. A water-free topical application composition for the treatment of nail diseases and nail care consisting essentially of:
   a) one or more antimycotic substances; and
   b) one or more $C_1$–$C_4$-alkyl esters of lactic acid, malic acid, tartaric acid or citric acid as carrier, wherein the carrier is a penetration promoting substance.

2. The topical application composition according to claim 1, wherein the carrier is selected from the group consisting of ethyl ester of lactic acid, malic acid, tartaric acid, citric acid, and mixtures thereof.

3. The topical application composition according to claim 1, wherein the carrier is selected from the group consisting of isopropyl esters of lactic acid, malic acid, tartaric acid, citric acid, and mixtures thereof.

4. The topical application composition according to claim 1, wherein the carrier is lactic acid ethyl ester.

5. A process for manufacturing a water-free topical application composition free of film or lacquer-forming additives, comprising the steps of:
   a) mixing one or more $C_1$–$C_4$-alkyl esters of lactic acid, malic acid, tartaric acid or citric acid; and
   b) dissolving one or more antimycotic substances in the mixture formed in step a) until a homogenous solution is obtained.

6. A method for treating nail disease(s), periungual disease(s) or providing nail care comprising the step of:
   applying to a nail the topical composition of claim 1.

7. A method for treating mycotic infections of the hoove(s), paw(s) or claw(s) of pets or domestic animals comprising the step of:
   applying the topical composition of claim 1 to the hoove(s), paw(s) or claws(s).

8. The topical application composition according to claim 1, further comprising one or more biologically active substances selected from the group consisting of antibiotics, antiseptics, corticosteroids and nutrient and anabolic substances.

9. The topical application composition according to claim 8, wherein the nutrient and anabolic substances are selected from the group of the amino acids, the vitamins and the mineral substances.

* * * * *